United States Patent [19]
Miyawaki et al.

[11] Patent Number: 6,066,151
[45] Date of Patent: May 23, 2000

[54] ULTRASONIC SURGICAL APPARATUS

[75] Inventors: Makoto Miyawaki, Tanashi; Mitsumasa Okada; Toshihiko Suzuta, both of Hachioji, all of Japan

[73] Assignee: Olympus Optical Co., Ltd., Tokyo, Japan

[21] Appl. No.: 09/207,731

[22] Filed: Dec. 8, 1998

[30]     Foreign Application Priority Data

Dec. 24, 1997  [JP]  Japan ................................. 9-355390

[51] Int. Cl.⁷ .................................................. A61B 17/32
[52] U.S. Cl. ................................................ 606/169; 606/205
[58] Field of Search .................................. 606/1, 32, 37, 606/39, 40, 41, 50–52, 135, 137, 167, 169, 205; 604/19, 22

[56]           References Cited

U.S. PATENT DOCUMENTS 5,322,055  6/1994  Davison et al. .
5,873,873  2/1999  Smith et al. ............................. 606/169
5,906,628  5/1999  Miyawaki et al. ...................... 606/169

*Primary Examiner*—Glenn K. Dawson
*Attorney, Agent, or Firm*—Frishauf, Holtz, Goodman, Langer & Chick, P.C.

[57]          ABSTRACT

An ultrasonic surgical apparatus of the present invention includes a vibration transmitting member for transmitting an ultrasonic vibration, a probe provided at a far end of the vibration transmitting member, a jaw adapted to grasp a tissue of interest relative to the probe, a jaw holding member movably supporting the jaw, an operation drive rod connected to the jaw, and an operation unit for operating the operation drive rod. A stopper tube is provided on the operation drive rod conductive to the opening/closing operation of the jaw and an opening/closing terminal position of the jaw relative to the probe is restricted by abutting the stopper tube against the jaw holding member.

15 Claims, 13 Drawing Sheets

ULTRASONIC SURGICAL APPARATUS

BACKGROUND OF THE INVENTION

The present invention relates to an ultrasonic surgical apparatus for, for example, cutting, removing, or coagulating a living tissue, by an ultrasonic wave, while grasping the tissue either internally (inside a body) or externally.

This type of the ultrasonic surgical apparatus is known in U.S. Pat. No. 5,322,055 for example. The ultrasonic surgical apparatus comprises an ultrasonic wave transmitting probe member connected to an ultrasonic transducer, a sheath inserted through the probe member, a blade coupled to a forward end of the robe member, a jaw pivoted to a distal end of the sheath and facing the blade, and a handle provided on a proximal end of the sheath and adapted to swing the jaw through a rod. And the jaw is swung by the operation of the handle and, while grasping a living tissue between the jaw and the blade, an ultrasonic vibration is transmitted to the jaw and, by doing so, the living tissue is cut. At this time, simultaneous coagulating and cutting actions are applied by the ultrasonic wave to the grasped tissue and it is possible to cut off only the grasped tissue without bleeding in a patient.

Normally, this type of ultrasonic surgical apparatus can apply both the coagulating and cutting actions to the tissue by one operation and it is possible to rapidly cut open the tissue of the patient without bleeding. This procedure is simpler than the method for cutting the living tissue by an existing surgical knife. And attention has been paid to applying this method to the cases where the organs in the body cavity of the patient are treated, in particular, by a surgical operation under an endoscope.

With this ultrasonic surgical apparatus, the jaw opposite to the blade on the forward end of the probe is moved in swinging motion and the living tissue is grasped between the jaw and the blade and cut open while being coagulated. There is a risk, however, that, if the living tissue is forcibly squeezed between the jaw and the blade by operating the handle more strongly than normally, it will be simply mechanically cut off without being cut open while being coagulated with the ultrasonic wave. For example, the living tissue of the liver, etc., is liable to be readily cut off mechanically.

When even very narrow blood vessels are to be coagulated and cut off, it is difficult to control an amount of force with which the handle is operated. The control amount of force applied by the handle differs from individual to individual and lots of practice have been required in operating the handle with a constantly steady, proper control force.

In the case where, though depending upon the power extent of the ultrasonic transducer, the living tissue is grasped rather strongly between the blade and the jaw, the vibration of the probe may be suppressed and sometimes stopped.

Further, the action area of the blade is situated at the antinode loop of the ultrasonic vibration and located at a free end remote from the support area of the probe corresponding to the node of the ultrasonic vibration. For this reason, the blade area is naturally a ready-to-flex area. When the tissue is grasped with a force exceeding that required, then the blade area is greatly flexed in a direction escaping from the jaw, thus resulting in an inconvenient position in which the grasping surface of the blade and that of the jaw intersect with each other without being parallel to each other, that is, the jaw is diagonally opposite to the blade. When, in a final tissue cutting stage in particular, the jaw is diagonally opposite to the blade, these grasping surfaces cannot grasp the tissue uniformly, so that no proper cut of the tissue is expected. That is, some of the tissue remains uncut and it is not possible to coagulate/cut a whole tissue of interest at a time.

BRIEF SUMMARY OF THE INVENTION

It is accordingly the object of the present invention to provide an ultrasonic surgical apparatus which, while grasping a tissue of interest, can positively treat it simply by a normal operation with a stable proper amount of force without requiring any particular skill.

Accordingly to the present invention, there is provided an ultrasonic surgical apparatus for treating a tissue of interest by applying an ultrasonic wave to the tissue while grasping the tissue between an ultrasonic probe and a jaw, comprising:

an ultrasonic transducer provided at a housing and generating an ultrasonic vibration;

a vibration transmitting member connected to the ultrasonic transducer to transmit the ultrasonic vibration;

an ultrasonic probe connected to the vibration transmitting member;

a movable jaw mounted relative to the probe and, together with the probe, grasping the tissue;

a movable member operated to remove the jaw;

a support member stationary relative to at least one of the jaw and movable member and supporting said at least one member; and a stopper adapted to, when the jaw is moved relative to the probe side, restrict a terminal position of the jaw by utilizing said at least one member and support member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

One embodiment of the present invention will be explained below with reference to the accompanying drawing.

Figure 1:
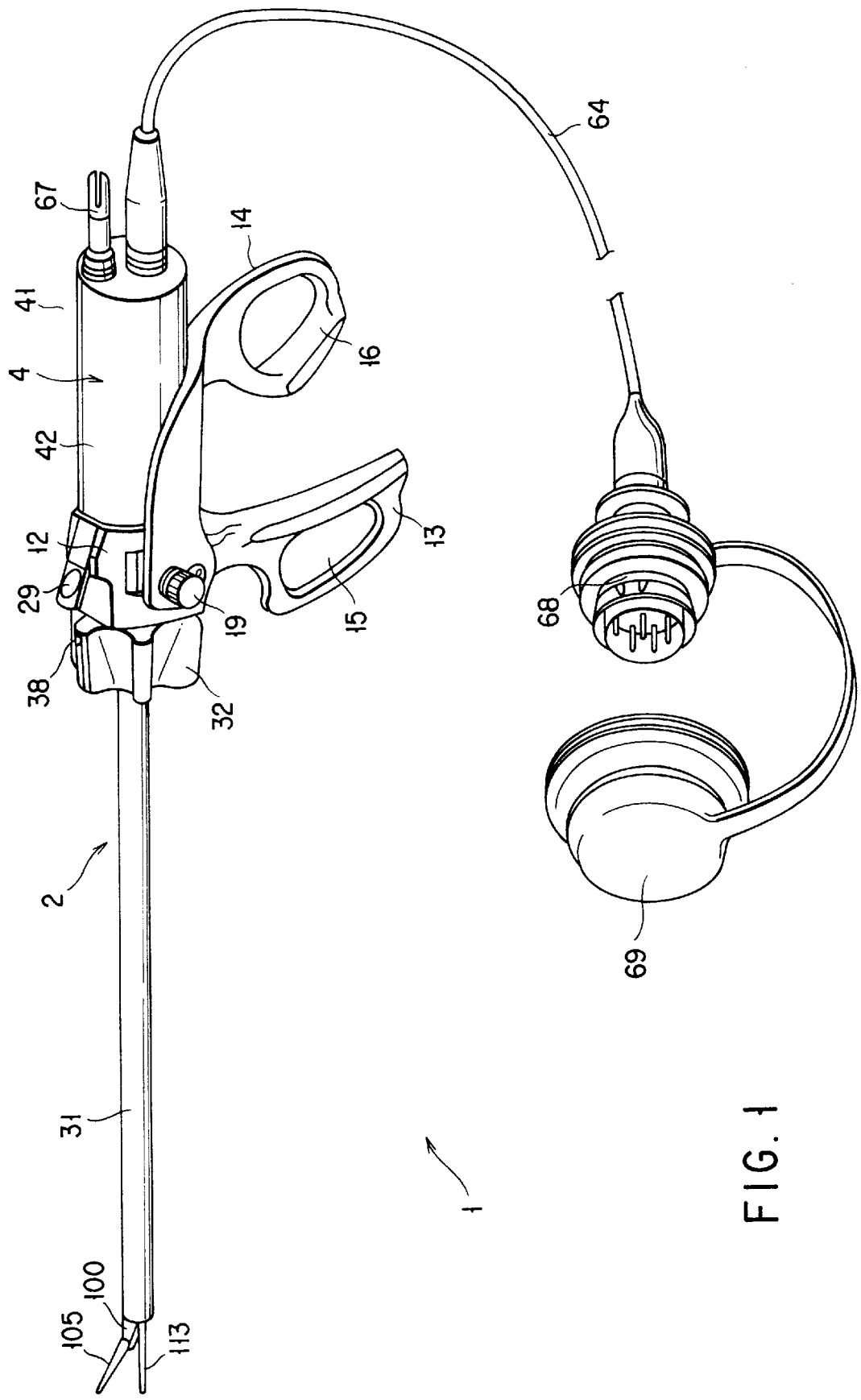
FIG. 1 is a perspective view showing an ultrasonic coagulating/cutting apparatus, in an assembled state, according to a first embodiment of the present invention.
Figure 2A:
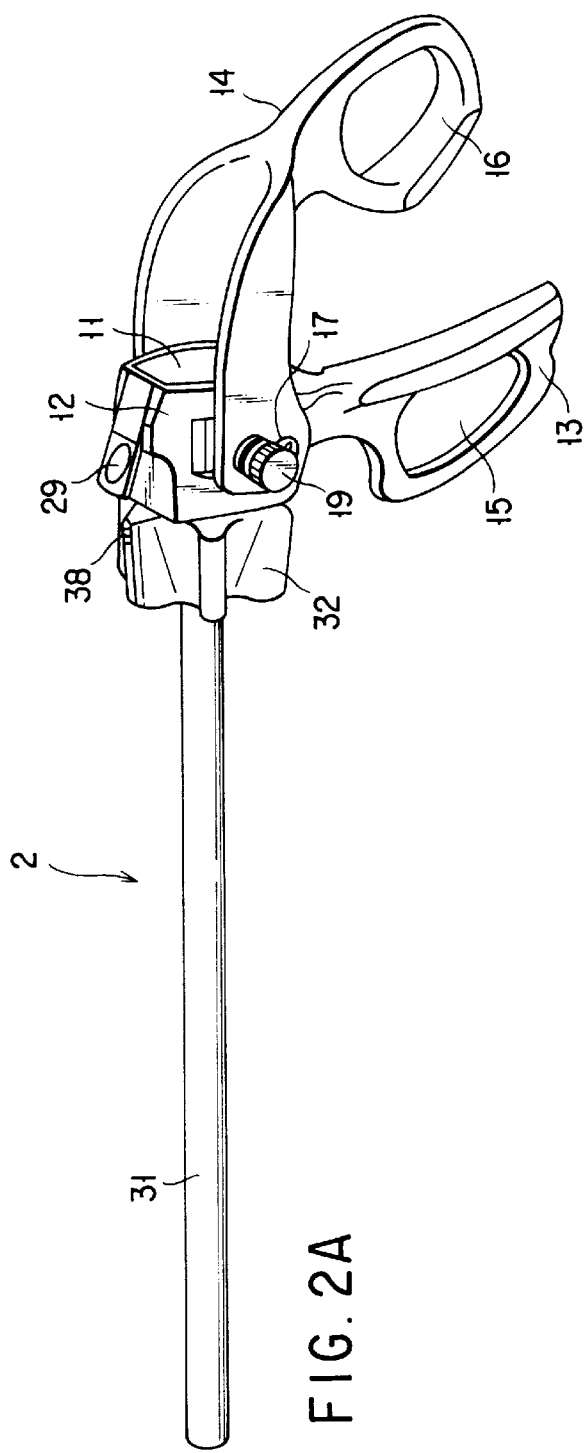
FIG. 2A is a perspective view showing a handle unit of the ultrasonic coagulating/cutting apparatus.
Figure 2B:
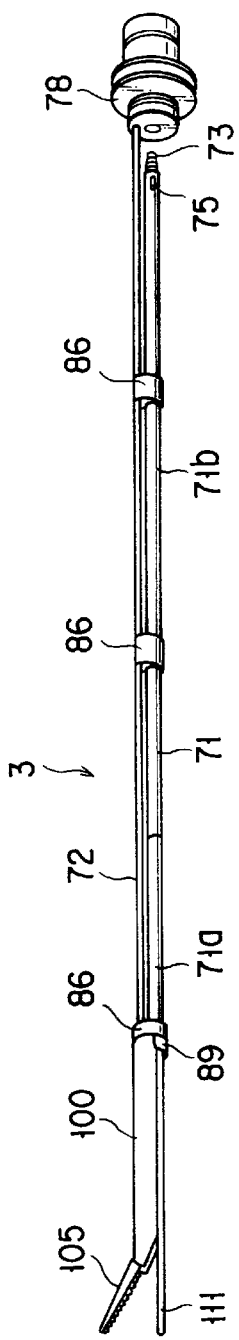
FIG. 2B is a perspective view showing a probe unit of the apparatus.
Figure 3:
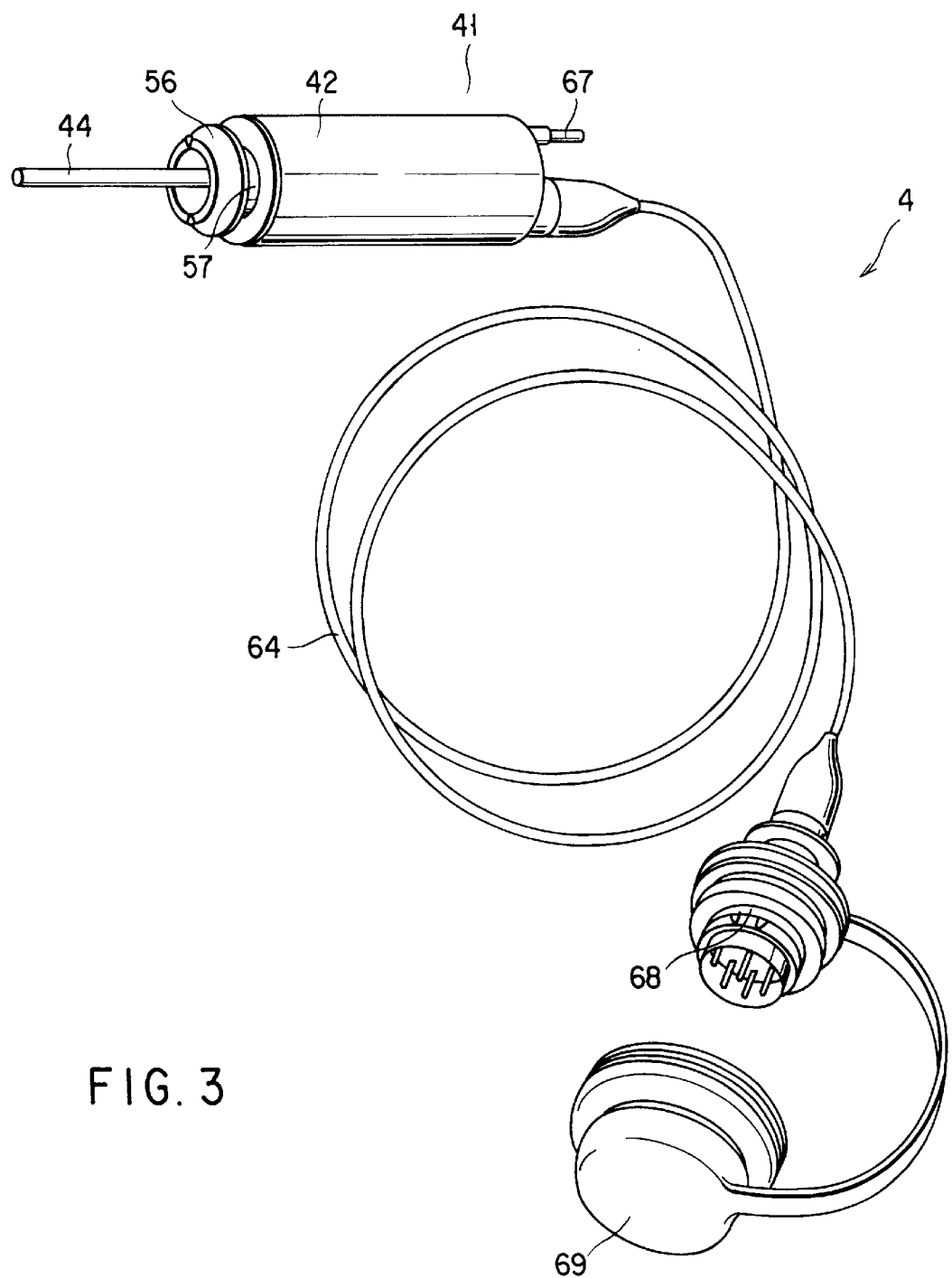
FIG. 3 is a perspective view showing a transducer unit of the apparatus.

An ultrasonic type coagulating/cutting instrument 1 includes a handle unit 2 shown in FIG. 2A, a probe unit 3 shown in FIG. 2B and a transducer unit 4 shown in FIG. 3. These units are assembled in a state shown in FIG. 1.

As shown in FIG. 2A, the handle unit 2 comprises an operation body section 12 equipped with a transducer connection section 11, a front-side handle 13 fixed to the operation body section 12, and a rear-side handle 14 swingably mounted on the operation body section 12. A ring section is provided in the operation end of the front-side handle 13 and has a finger engaging hole 15. The finger engaging hole is so formed as to selectively insert any fingers other than the thumb therein. A ring section is provided at the operation end of the rear-side handle 14 and has a thumb engaging hole 16 to allow the thumb of the same hand to be inserted therein. The base end portion of the rear-side handle 14 is pivoted by an axial pin 17 (see FIG. 5) threaded in the operation body section 12, so that the rear-side handle 14 can be swung about the axial pin 17.

Figure 5:
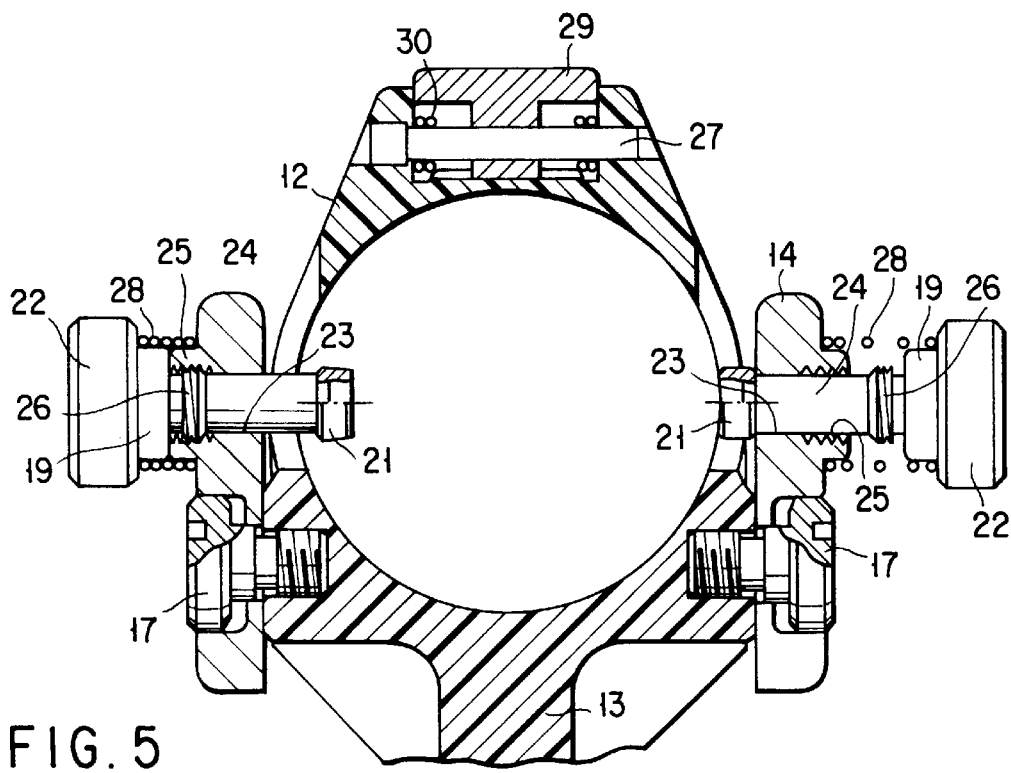
FIG. 5 is a cross-sectional view showing the handle unit of the apparatus.

As shown in FIGS. 2 and 5, a fixed screw member 19 is provided on the base end portion of the rear-side handle 14 and serves also as an engaging pin. In a position somewhat remote from the axial pin 17, the fixed screw member 19 extends through a through hole 23 in the rear-side handle 14. An engaging section 21 is provided at the inner end of the fixed screw member 19 and engages with a probe unit 3 mounted on the operation body section 12. An operation knob 22 is formed on the other end of the fixed screw member 19. The intermediate portion of the fixed screw member 19 provides a play portion 24 freely movable in the through hole 23. And the fixed screw member 19 has its play portion 24 positioned in the through hole 23 and freely movable in the axial direction of the fixed screw member 19 relative to the rear-side handle 14. In the intermediate section of the fixed screw member 19, an externally threaded section 26 is provided at an outer side than the play portion 24 so as to be threaded on a internally threaded section 25 provided in the wall of the through hole 23. The fixed screw member 19 has its play portion 24 moved back and forth over a range in which the play section 24 is located in the through hole 23. For this reason, the engaging section 21 has its engaged portion released by being retracted from a position engaged with a rotor 78 as will be described later and the engaging section 21, being advanced into an engaged position, allows the externally threaded section 26 of the fixed screw member 19 to be threaded into the internally threaded section 25, so that it is fixed to the position engaged with the rotor 78.

A spring member, such as a coil spring 28, is wrapped around the fixed screw member 19. The coil spring 28 is located between the rear-side handle 14 and the operation knob 22 to allow both to be urged in a direction apart from each other. When the externally threaded section 26 is removed from the internally threaded section 25, the fixed screw member 19 is automatically retracted from a later-described rotor 78 side, as indicated by a right side in FIG. 5, under an elastic restoring power. For this reason, the arrangement allows the probe unit 3 to be inserted/attached and detached/withdrawn.

A stopper piece 29 is pivoted on the operation body section 12 and fixes the transducer unit 4, which is mounted on the operation body section 12, in a predetermined position. As indicated in FIG. 5, the stopper piece 29 is urged by a coil spring 30 provided around a pivoting shaft 27, so that it is swung in a direction to latch the transducer unit 4. Normally, the stopper piece is swung in a direction of an arrow in FIG. 4A to a position indicated by a solid line.

Figures 4A, 4B:
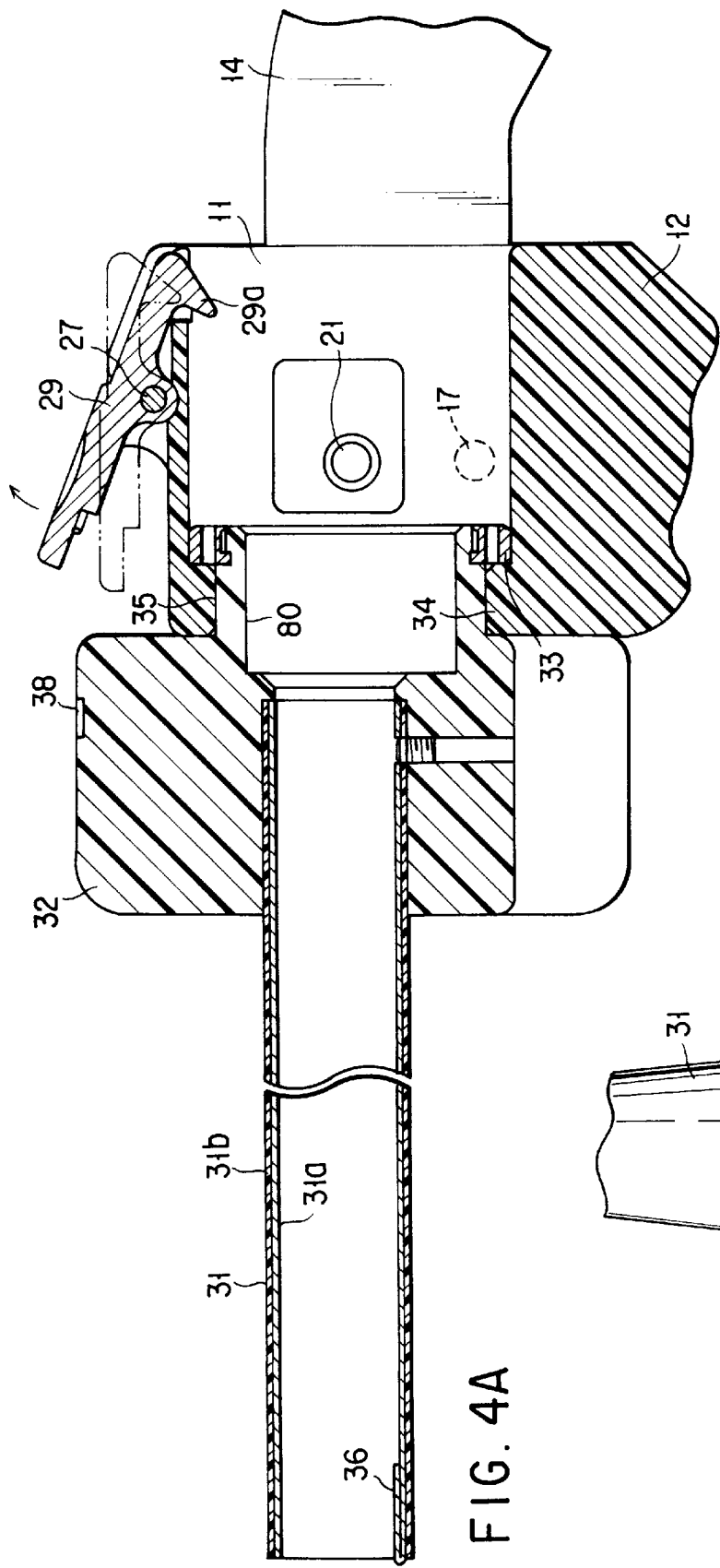
FIG. 4A is a longitudinal cross-section showing a handle unit of the apparatus.
FIG. 4B is a perspective view showing a distal end section of an insertion sheath in the handle unit of the apparatus.

As shown in FIG. 4A, an insertion sheath 31 is rotatably connected to the forward end portion of the operation body section 12 by utilizing the rotation knob 32 and fastening nut 33. The insertion sheath 31 is rotatably supported on the operation body section. That is, the insertion sheath 31 is fixedly mounted on the rotation knob 32 and the rotation knob 32 is coaxially and rotatably mounted at the operation body section 12. The rotation knob 32 is rotatably retained by sandwiching a collar 34 on the operation body section 12 between the rotation knob 32 and the fastening nut 33. The structure above provides a bearing means 35 for supporting the insertion sheath 31.

The insertion sheath 31 is normally braked to some extent due to a friction force acting by a member with which the rotation knob 32 is slidably contacted. As a result, the insertion sheath is not readily operated in a simpler way. When, however, a strong hand grip is made between the front-side handle 13 and the rear-side handle 14, a pressure force increased therebetween, so that an increased frictional force and hence a brake act there. The operation body section 12 has a function of braking the rotation of the insertion sheath 31.

As shown in FIG. 4A, the insertion sheath 31 has a double structure comprising a core member 31a of a rigid metal pipe and an outer cover 31b of an electrically insulating resin. As shown in FIG. 4B, a pair of latching pieces 36 are provided at the distal end of the insertion sheath 31 such that they are inside the insertion sheath. The latching pieces 36 engages with the distal end portion of the probe unit 3 inserted in the insertion sheath 33 and determines the position of the probe unit 3 relative to the insertion sheath 31. The latching pieces 36 are formed by a pair of bent extension portions of the distal end of the core member 31a. An index 38 showing the latching position is provided on the outer surface of the rotation knob 32 corresponding to the position of the latching pieces 36. If, with the index 38 set in an upper position, the probe unit 3 is inserted into the operation body section 12 in a manner to set its posture in an up/down direction, a later-described jaw retaining member provided at the forward end of the probe unit 3 is partially latched to the latching pieces 36. Simultaneously therewith, the stopper piece 29 of the operation body section 12 fixes a portion of the handpiece 41 of the transducer unit 4 in place. By doing so, it is possible to position the probe unit 3 relative to the insertion sheath 31 and mount it in place.

Figure 7A:
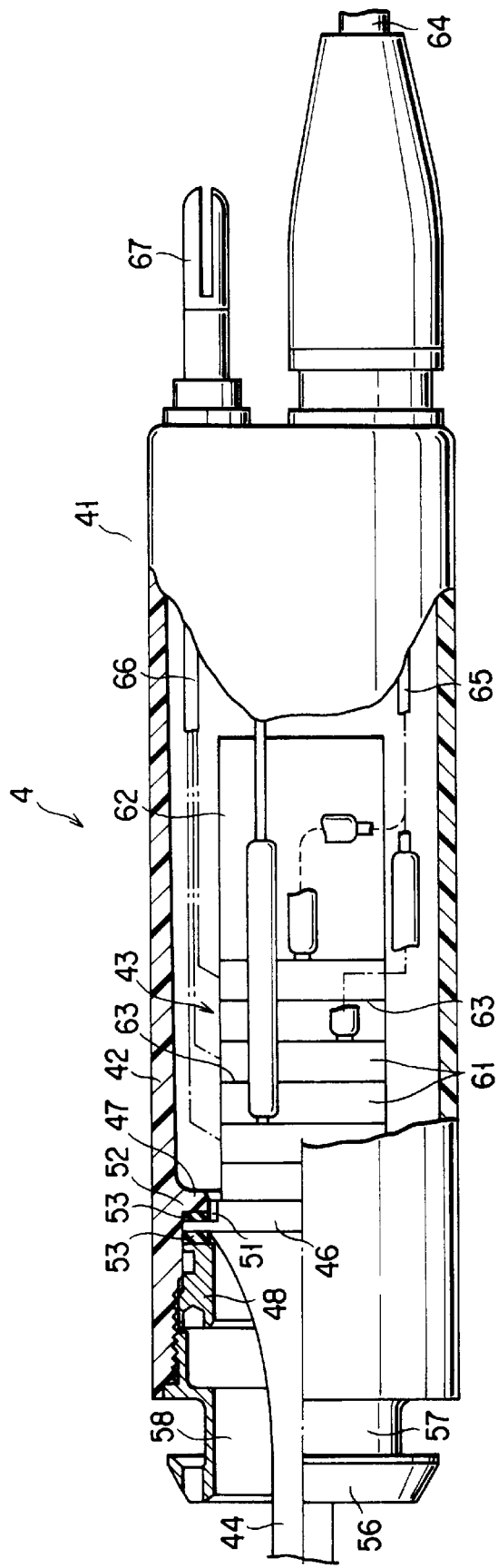
FIG. 7A is a view, partly broken away and partly in section, showing the transducer unit.
Figure 7B:
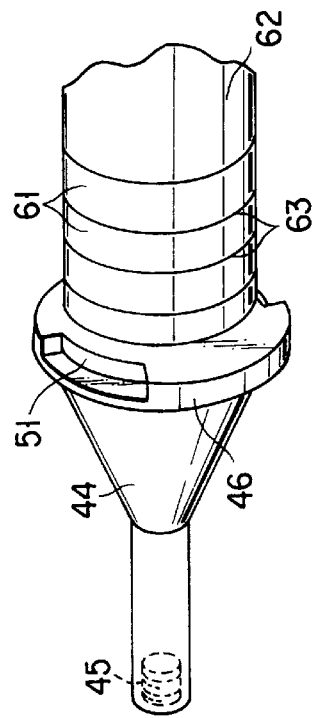
FIG. 7B is a perspective view showing ultrasonic vibration elements.

As shown in FIG. 7A, the transducer unit 4 has a Langevin type transducer 43 positioned in a cylindrical cover 42 serving as a housing of the handpiece 41 and a horn 44 connected to the forward end of the transducer 43. As shown in FIG. 7B, an internal thread portion 45 is provided at the forward end of the horn 44 to allow the rear end portion of the probe unit 3 to be threaded therein. By supporting the horn 44 at the forward end of the cover 42, the transducer 43 is held through the horn 44. An outer collar 46 is provided at the rear end of the horn 44 and closely fitted in the inner wall of the cover 42. The outer collar 46 is fixed in place by being sandwiched between the inner collar 47 formed on the inner wall of the cover 42 and a fixed ring 48 threaded on the cover 42 and, by doing so, the horn 44 is held in place.

As shown in FIG. 7B, an engaging receiving section 51 is provided, as a cutout recess, in a portion of the outer collar 46 of the horn 44. On the other hand, an engaging section 52 is provided as a projection placed in fitting engagement with the engaging receiving section 51. The outer collar 46 of the horn 44 is sandwiched between the inner collar 47 on the cover 42 side and the fixed ring 48 as viewed in the axial direction of the horn 44 in such a way as to have a cushioning member 53 interposed as an elastic member there. That is, the horn 44 is elastically supported by the cushioning member 53 relative to its axial direction.

As shown in FIG. 7A, a ring-like stopper receiving member 56 is threadably mounted on the forward end of the cylindrical cover 42. An annular peripheral groove 57 is provided in the outer peripheral portion of the stopper receiving member 56. The stopper piece 29 on the handle unit 2 side is fitted into, and latched to, the annular peripheral groove 57 in the stopper receiving member 56. The rear end portion of the rotor 78 of the probe unit 3 is fitted into an inner bore 58 of the stopper receiving member 56.

As shown in FIG. 7A, the transducer 43 comprises a plurality of stacked piezoelectric elements 61 arranged between the horn 44 and the rear member 62 and fastened by a bolt, not shown, passed through their center areas. An electrode 63 is provided between the piezoelectric elements 61. Through the respective electrodes 63 a drive voltage is applied to the Respective piezoelectric elements 61. Lead-in wires 65 from a handpiece code 64 are connected to the electrodes 63 on the active side. Another lead-in wires 66 are connected to the electrodes 63 on the ground side. The lead-in wires 66 are connected to a connection pin 67 for high frequency. To the connection pin 67 is connected a high-frequency supply cord, not shown, leading to a high-frequency power source. The electrodes 63 on the ground side are electrically connected to the conductive horn 44 from the conductive bolt of the transducer 43. Further, the later-described vibration transmitting member and probe of the probe unit 3 connected to the forward end of the horn 44 are also made of a conductive material. Through these members, an electrical connection is made up to the treating section at the distal end side.

As shown in FIG. 3, the handpiece cord 64 is greater in length and flexible and a handpiece plug 68 is connected to the extending end of the cord 64. A water-proof cap 69 is attached to the handpiece plug 68. The transducer unit 4, when being washed, is covered with the water-proof cap 69.

The probe unit 3 is so structured as shown in FIGS. 8A to 10H. That is, the probe unit 3 has a rod-like vibration transmitting member 71 for transmitting an ultrasonic vibration and wire-like operation drive rod (movable member) arranged along and substantially parallel to the vibration transmitting member. The vibration transmitting member 71 is made of a material of a higher acoustic effect and better biocompatibility, such as titanium and aluminum. The vibration transmitting member 71 is comprised of a two-part member consisting of a distal-end section 71a and rear-end section 71b fixedly joined by an adhesive and threading means. As shown in FIG. 9B, an externally threaded section 73 is formed at the rear-end portion of the vibration transmitting member 71. The externally threaded section 73 is screw-threaded into the internally threaded section 45 provided at the forward end portion of the horn 44. This is done up to a position in which a stepped face 74 at the rear end of the vibration transmitting member 71 abuts against the forward end face of the horn 44. By doing so, the vibration member 71 is strongly connected to the horn 44. A spanner engaging face 75 is formed on the outer peripheral surface of the rear end section of the vibration transmitting member 71. A spanner's head opening as will be set out below may be engaged with the spanner engaging surface 75.

The operation drive rod 72 is made up of a wire-like member and has not only a relatively rigid property but also an elastic property. The operation drive rod 72 is made of a material such as a stainless steel (SUS) and is fitted over a thinner metal pipe 76. The pipe 76 is closely fitted over an area ranging from the base end to a near-distal-end of the operation drive rod. The pipe 76 is adhesively bonded to the outer periphery of the operation drive rod 72. A small cutout 77 is formed at a proper place in the pipe 76 and the adhesive is injected via the opening of the cutout 77, so that the pipe 76 is bonded to the rod 72.

Figure 9A:
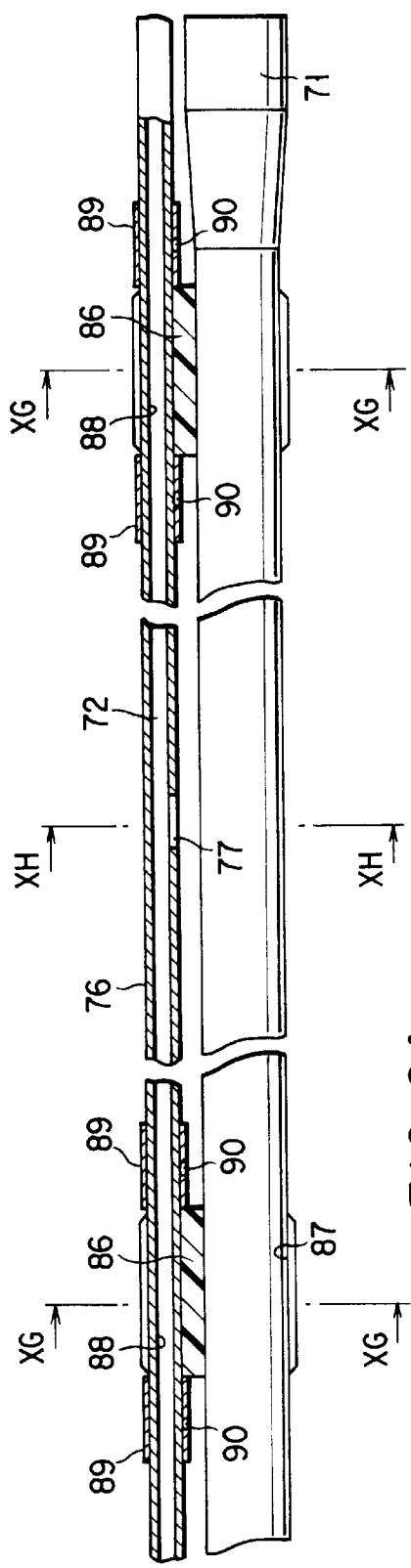
FIG. 9A is a longitudinal cross-sectional view showing a rear-end section following the intermediate section of the probe unit.
Figure 9B:
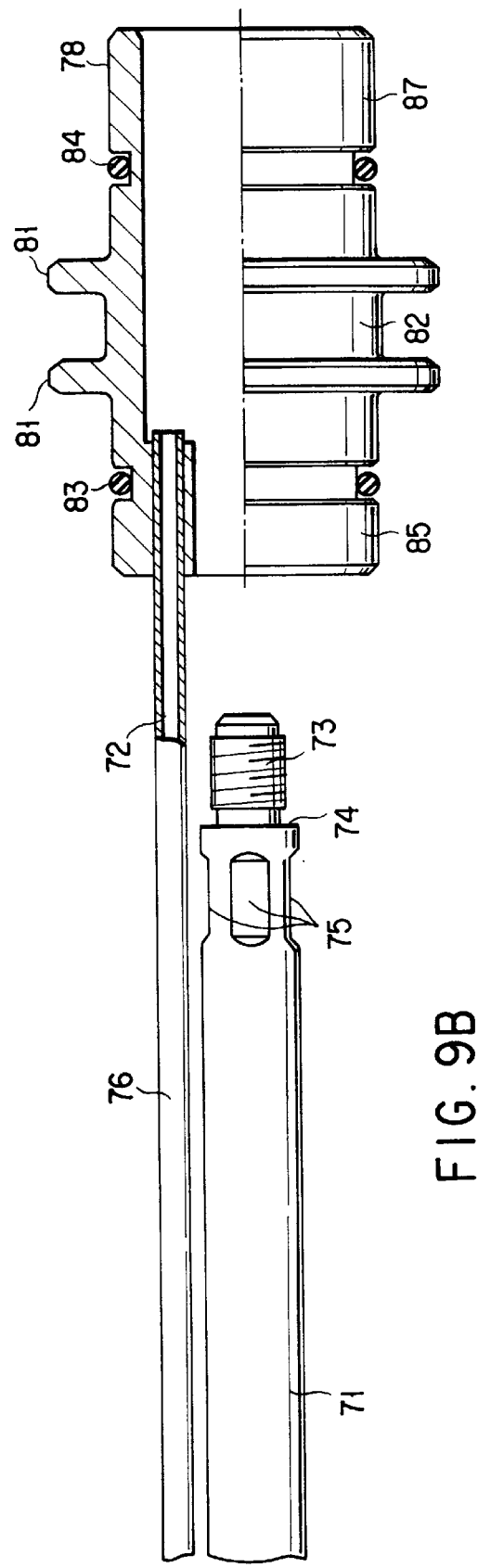
FIG. 9B is a longitudinal cross-sectional view showing the rear end section of the probe unit.

As shown in FIG. 9B, a rotor 78 is fixedly mounted on the rear end portion of the operation drive rod 72. The rotor 78 constitutes a cylindrical rotary unit whose center axis aligns with the center axis of the vibration transmitting member 71. A pair of collars 81, 81 are provided on the outer periphery of the rotor 78 with an annular groove 82 defined therebetween. The engaging portion 21 of the fixing screw member 19 mounted on the rear-side handle 14 at the handle unit 2 is fitted in the annular groove 82. O-rings 84 are provided one before and one after the annular groove 82.

Upon an assembly of the respective units, a forward-end side peripheral portion 85 of the rotor 78 is fitted into a fitting bore 80 of the handle unit 2 and the rear-end side peripheral portion of the rotor 78 is fitted into the inner bore 58 of the stopper receiving member 56. And the stopper piece 29 is latched onto the annular peripheral groove 57 of the stopper receiving member 56 on the transducer unit 4 side. The transducer unit 4 together with the probe unit 3 can be rotated as one unit. The operation drive rod 72 of the probe unit 3 together with the rotor 78 can be moved, by the handle operation of the handle unit 2, as one unit in a back-and-forth direction relative to the stationary members of the transducer unit 4 and vibration transmitting member 71.

The vibration transmitting member 71 and operation drive rod 72 are held in place by a plurality of spacers 86. The respective spacers 86 are located at those positions corresponding to the nodes of the vibration of the vibration transmitting member 71. The spacer 86 has the fitting groove 87 through which the intermediate portion of the vibration transmitting member 71 is slidably fitted and a support hole (fitting groove) 88 through which the pipe 76 fitted over the operation drive rod 72 extends. The vibration transmitting member 71 and operation drive rod 72 are held at a predetermined distance in a parallel relation. Retaining rings 89 are fitted over the operation drive rod 72 one before and one after each spacer 86 except the forwardest spacer. By doing so, the spacer 86 is prevented from being displaced in the back- and forth direction. The respective retaining ring 89 is fixed by the adhesive to the outer periphery of the pipe in which the operation drive rod 72 is fitted. Slits 90 are formed in the retaining ring 89 to allow the adhesive to be injected therethrough.

That spacer 86 at the forwardest position is located in a position corresponding to the node of an ultrasonic vibration nearest to the remotest position member including a later-described probe 113. This spacer 86 may be bonded to the outer peripheral surface of the pipe 76 fitted over the operation drive rod 72, but, here, it is simply fitted over the outer periphery of the pipe 76. The forwardest position spacer 86 has the support member 92 and, together with the support member 92, is covered with a retaining ring 91, so that both are tightened and bonded/fixed as an integral unit. The portion of a later-described flange 95 of the vibration transmitting member 71 is sandwiched by the spacer 86 and support member 92 from both sides. By doing so, the retaining ring 91 is closely fitted over a unit of both the spacer 86 and support member 92 and a bond is created between the spacer 86 and the retaining ring 91. At this time, both the support 92 and the spacer 86 may be bonded/fixed together.

Figure 10A:
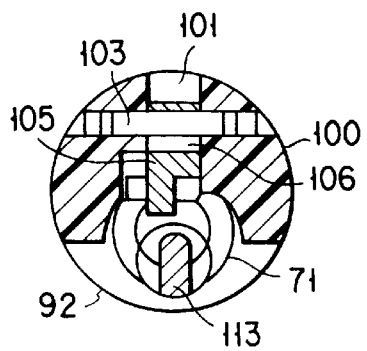
FIG. 10A is a cross-sectional view, as taken along line XA—XA in FIG. 8A, showing a portion of the probe unit.
Figure 10B:
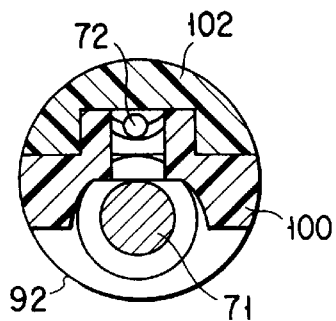
FIG. 10B is a cross-sectional view, as taken along line XB—XB in FIG. 8A, showing a portion of the probe unit.
Figure 10C:
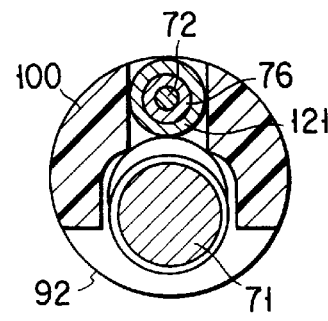
FIG. 10C is a cross-sectional view, as taken along line XC—XC in FIG. 8, showing a portion of the probe unit.
Figure 10D:
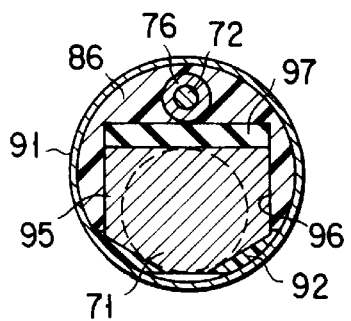
FIG. 10D is a cross-sectional view, as taken along line XD—XD in FIG. 8A, a portion of the probe unit.
Figure 10E:
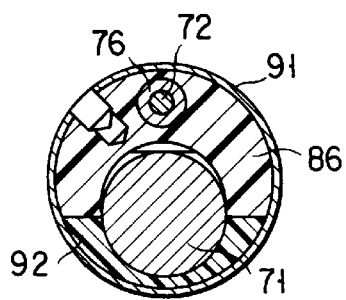
FIG. 10E is a cross-sectional view, as taken along line XE—XE in FIG. 8A, showing a portion of the probe unit.
Figure 10F:
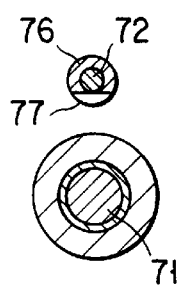
FIG. 10F is a cross-sectional view, taken along line XF—XF in FIG. 8B, showing a portion of the probe unit.
Figure 10G:
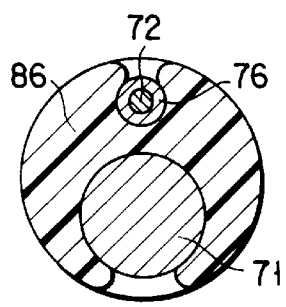
FIG. 10G is a cross-sectional view, taken along line XG—XG in FIG. 9A, showing a portion of the probe unit.
Figure 10H:
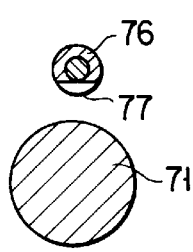
FIG. 10H is a cross-sectional view, as taken along line XH—XH in FIG. 9A, showing a portion of the probe unit.

As shown in FIG. 10D, the flarge 95 for rotation restriction is created at the portion of the vibration transmitting member 71 situated at the forwardest position spacer 86. The flange 95 has a different rectangular shape in cross-section and is closely fitted in a fitting groove 96 in the inner surface of the corresponding spacer 86, so that it prevents the spacer 86 from being rotated about the vibration transmitting member 71. Between the rotation restriction flange 95 and the spacer 86 a cushion member 97 of, for example, rubber is fitted as a vibration absorbing member in the fitting groove 96 of the spacer 86 on the operation drive rod 72 side.

The forwardest position spacer 86 also acts as a support base of a jaw holding member 100 extending forwardly of the spacer's position. Both the spacer 86 and the jaw holding member 100 are formed as an integral unit. By doing so, the jaw holding member 100 is restricted from being moved in the axial direction of the vibration transmitting member 71 and being rotated around its axis. The jaw holding member 100 has its forward end extending just to the distal end of the vibration transmitting member 71. A jaw 105 is connected near the distal end of that extending forward end. A slit groove 101 is provided from near the base end to the distal end of the jaw holding member 100. A reinforced bridge 102 is spanned between the right and left portions of the slit groove 101 at a location near the distal end of the jaw holding member 100.

Figures 8A, 8B:
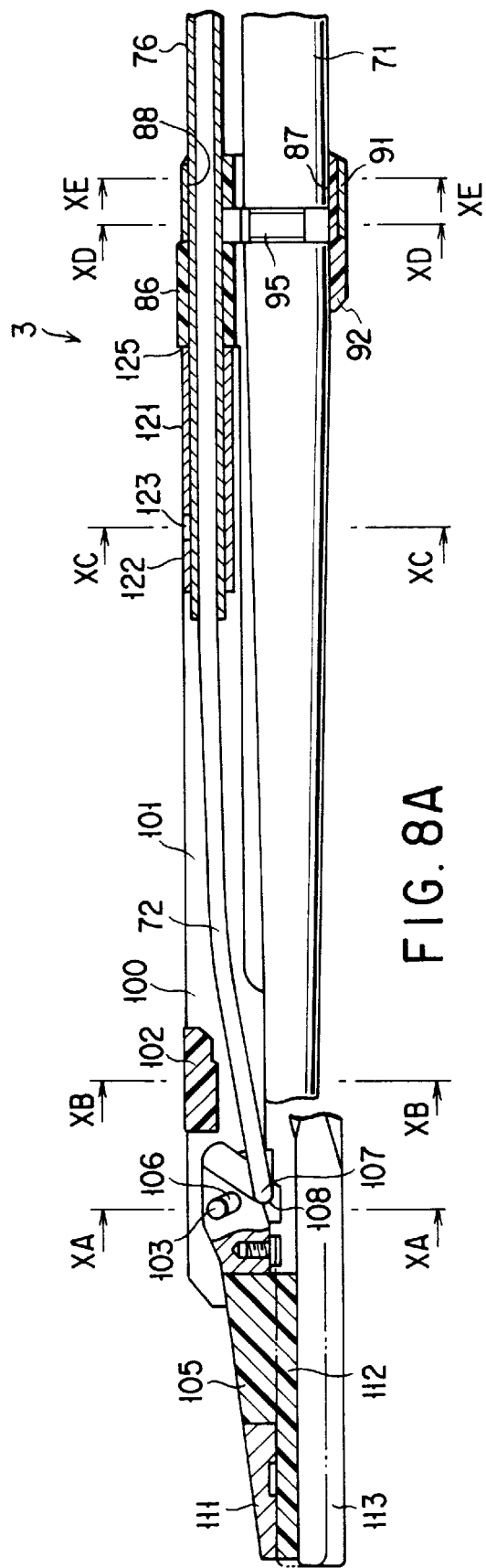
FIG. 8A is a longitudinal cross-sectional view showing a distal end section of the probe unit.
FIG. 8B is a longitudinal cross-sectional view showing an intermediate section following the distal end section of the probe unit.

A pivotal pin 103 is spanned cross the right and left portions of the slit groove 101 forwardly of the position of the reinforced bridge 102 and on the forward end portion of the jaw holding member 100. The jaw 105 is pivotally mounted about the pivotal pin 103. A bearing coupling hole 106 is provided in the base end portion of the jaw 105 and the pivotal pin 103 extends through the hole 106. Here, the hole 106 defines an oblique elongated hole 106 as shown in FIG. 8A. The pivotal pin 103 extends through the hole 106 to allow it to be freely moved along the longitudinal direction of the elongated hole.

A hole 108 is provided in the basic end portion of the jaw 105 on the lower side of the hole 106. With the distal end portion of the operation drive rod 72 inserted in the hole 18, the operation drive rod 72 is coupled there. The distal end portion of the operation drive rod 72 is bent at a substantially right angle with a bent section 107 fitted in the hole 108 (see FIG. 11). The length (width) of the bent section 107 is somewhat shorter than the width of the slit groove 101 shown in FIG. 10A. The bent section 107 is normally set in the slit groove 101. Even if the bent section 107 is assumed broken from its base, its broken piece will not fall in a body cavity, etc., of a subject since the bent section 107 is maintained in the hole 108 of the jaw 105.

The jaw 105 comprises a base body 111 and contact member 112 and these are assembled as an integral unit. The jaw 105 is set opposite to the ultrasonic probe (fixed-side grasping piece) 113 which is formed using the vibration transmitting member 71 directly. This provides what is called a movable blade (movable grasping piece).

As shown in FIG. 10A, the section of the probe 113 provides what is called as a fixed-side blade whose transverse cross-section defines are elongated shape. The probe 113 is rounded at the outer periphery of the distal end side. The jaw 105 is swung opposite to, and relative to, the probe 113 by pushing and pulling the operation drive rod 72. This provides a coagulating/cutting type ultrasonic treating unit by which a living tissue is grasped by the openable/closable jaw 105 and probe 113. FIG. 8 shows a closed state of the jaw 105 set by pulling the operation drive rod 72 and, in this state, the jaw 105 is wholly contacted with the upper surface of the probe 113.

Figures 11, 12A, 12B, 12C:
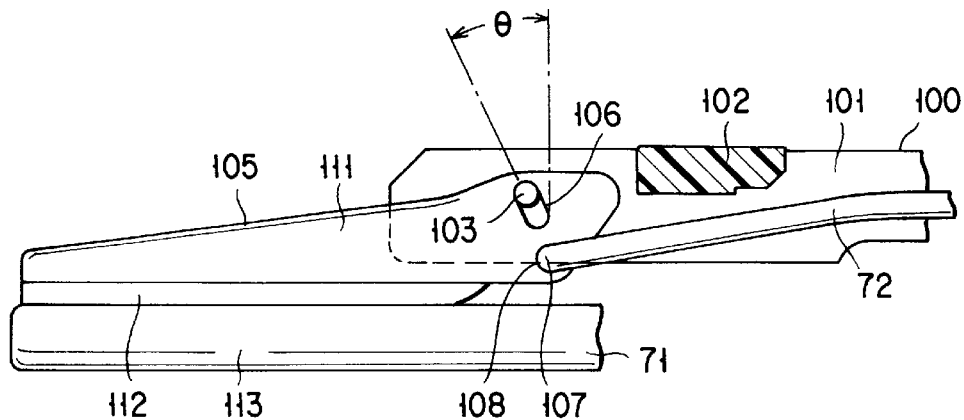
FIG. 11 is an explanatory view showing a distal-end treating section of the probe unit.
FIGS. 12A to 12C, each, are an explanatory view showing a distal-end treating section of the probe unit.

As shown in FIG. 11, the coupling hole 106 of the jaw 105 has an elongated configuration for allowing the pivotal pin 103 to be fitted therein. The longitudinal direction of the hole 106 is tilted at an angle θ to a line extending toward the hole 106 side in a relation perpendicular to the grasping surface of the probe 113. The longitudinal direction of the coupling hole 106 is inclined relative to a line defined, on the hole 106 side, in a relation perpendicular to the grasping surface, that is, a line passing through one end of the hole 106 situated on the grasping surface side of the jaw 105. By doing so, it is possible to improve a jaw-to-probe biting because the pivotal pin 103 is relatively moved in the hole 106 of the jaw. For the same reason, it is possible to increase an amount of operation stroke in a uniform biting between the jaw 105 and the probe 113 and ensure such a uniform biting over a whole length when the jaw is closed relative to the probe.

In the case of the present embodiment, the inclination angle θ of the hole 106 is set to 0°<θ<90°. Further, the inclination angle θ is desirably set to θ≦45° and, if it is set to 12°±10° in particular, then the grasping amount is set substantially equal both on the forward end side and on the proximal side.

The relation of the coupling hole 106 and pivotal pin 103 supporting the jaw 105 may be such that the pivotal pin 103 is provided on the jaw 105 side and the coupling hole 106 on the jaw holding member 100 side. In this case, the same function as set out above is also obtained.

A stopper mechanism is provided at the location of the jaw holding member 100 so as to restrict the amount of rotation of the jaw 105 when the rotating operation is effected, by pulling the operation drive rod 72, to set the jaw 105 to a closed position. That is, as shown in FIG. 8A, a stopper 121 is fitted over a portion of the operation drive rod (movable member) 72 situated in the slit groove 101 in the jaw holding member 100. A stopper tube 121 has an internally threaded portion in its inner wall in which the externally threaded portion on the outer peripheral wall of the pipe 76 fitted over the operation drive rod 72 is inserted. This mounting means is by the threadable mounting means and it is possible to effect a minor adjustment of the position of the stopper tube 121 during the mounting step of operation. A tubular nut 122 is threaded over an externally threaded portion on the outer peripheral surface of the pipe 76. The stopper tube 121 is fixed by a nut means 122 in a double-nut relation. A knurled surface is formed on the outer periphery of the stopper tube 121 and nut 122 to prevent a slippage when they are rotated. After the stopper tube 121 and nut 122 have these threaded positions adjusted on the pipe 76, they are bonded to the outer periphery of the pipe 76 and fixed in place, noting that a slit 123 for injecting an adhesive is provided in the stopper tube 121 and nut 122.

In the stopper mechanism, when the jaw 105 is closed by pulling the operation drive rod 72, the rear end of the stopper tube 121 abuts against a stopper receiving face 125 defined by a rear end face of the slit groove 101 in the stationary member side, so that further pull operation is prevented and hence an amount of operation by the jaw 105 is restricted. Since the stopper tube 121 is threadably mounted on the operation drive rod 72, the position of the stopper tube 121 relative to the operation drive rod 72 can be so adjusted as to cancel any error among the associated parts upon assembly. As a result, it is possible to accurately mount the stopper tube 121 in place.

Figure 14:
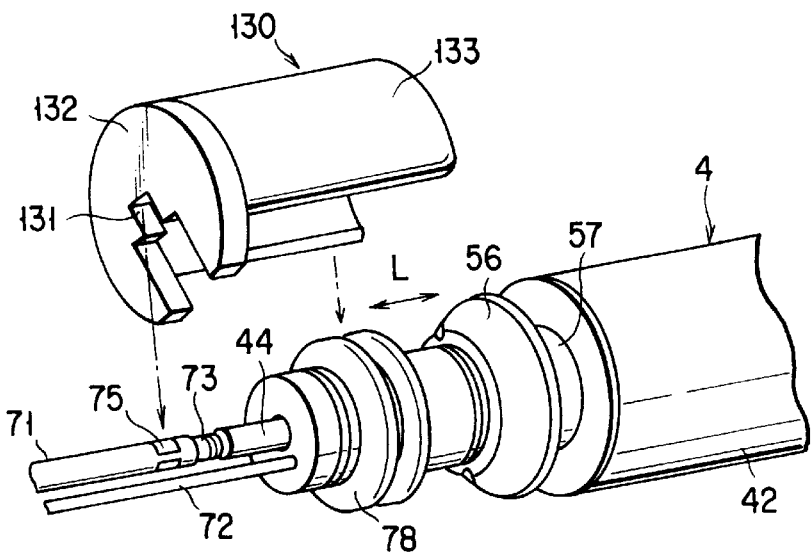
FIG. 14 is an explanatory view showing an assembly step of the probe unit and transducer unit.
Figure 15:
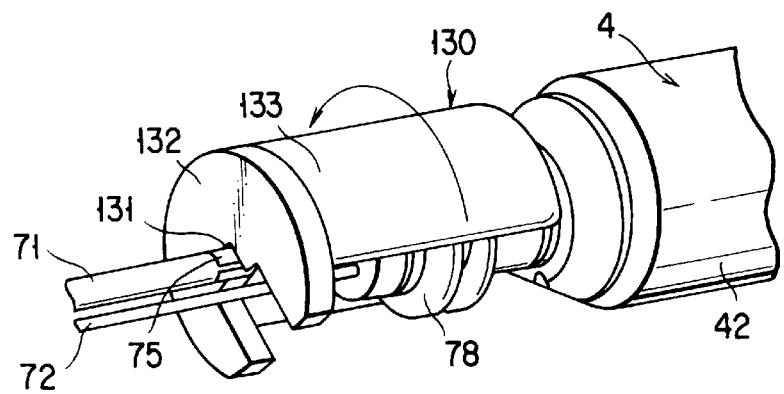
FIG. 15 is an explanatory view showing an assembly step of the probe unit and transducer unit.

In the ultrasonic type coaguliating/cutting instrument 1, a probe fastening spanner 130 as shown in FIGS. 14 and 15 is prepared. The spanner 130 comprises a spanner member 132 having an opening 131 engageable with the spanner engaging surface 75 on the vibration transmitting member 71 of the probe unit 3 and a grip section 133 for holding the spanner. The grip section 133 can grip the portion of the rotor 78 of the probe unit 3 in a circumferential direction. The grip section 133 comprises a core member as a metal member and a member of a high frictional coefficient such as a resin material. The grip section 133 grips the outer periphery of the rotor 78 by its inner surface.

Figure 13:
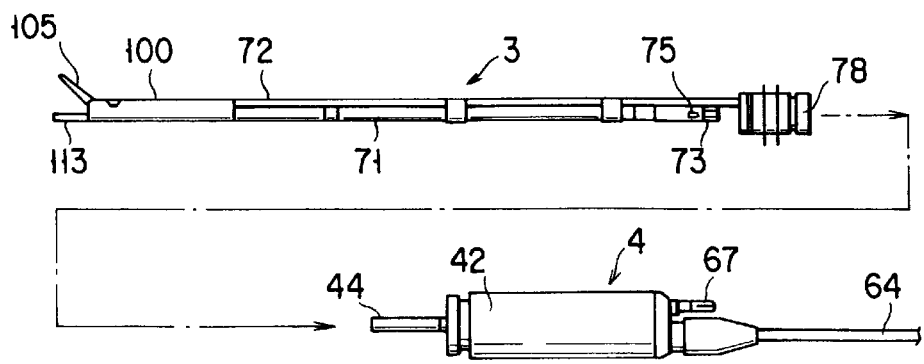
FIG. 13 is an explanatory vies showing an assembly step of the probe unit and transducer.

Now, an explanation will be given about the assembling process of the ultrasonic type coagulating/cutting instrument 1. As shown in FIG. 13, the horn 44 of the transducer unit 4 is inserted into the bore of the rotor 78 of the probe unit 3. As shown in FIGS. 14 and 15, the opening 131 of the spanner 130 is engaged with the spanner engaging surface 75 of the vibration transmitting member 71 and the grip section 133 is covered around the outer periphery of the rotor 78. Then the vibration transmitting member 71 is rotated while gripping the spanner 130 and the externally threaded section 73 is threadably mounted in the internally threaded section 45 of the horn 44.

Figure 16:
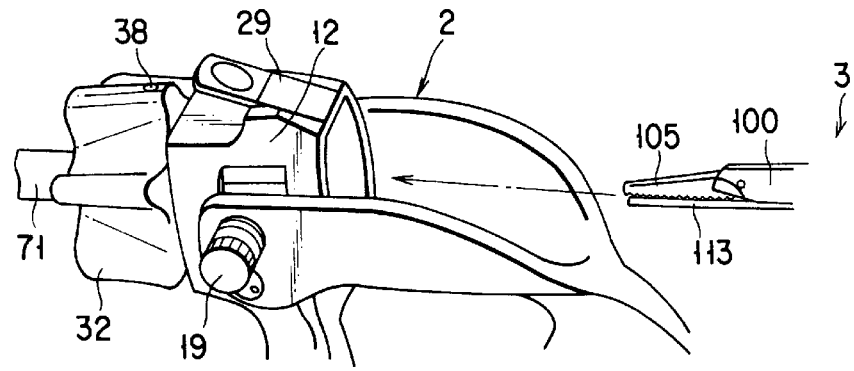
FIG. 16 is an explanatory view showing an assembly step of the probe unit and handle unit.
Figure 17:
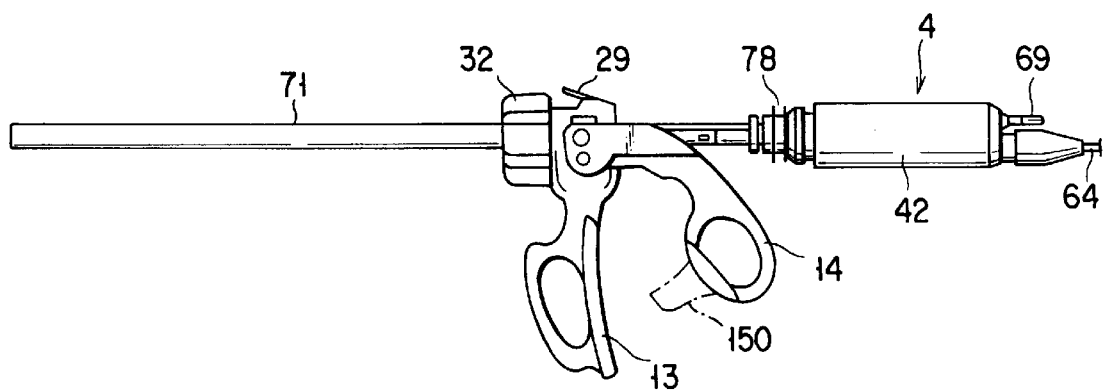
FIG. 17 is an explanatory view showing an assembly step of assembling the probe unit and transducer unit on the handle unit.

As shown in FIGS. 16 and 17, the probe unit 3 with the transducer unit 4 mounted thereon is inserted into the bore of the operation body section 12 of the handle unit 2. When the vibration unit 4 is inserted to a given depth, a claw 29a of the stopper piece 29 automatically drops in the annular peripheral groove 57 of the stopper receiving member 56, so that the transducer unit 4 is set in engagement with the operation body section 12. At this time, the front-end side periphery section 85 of the rotor 78 is fitted into the fitting bore 80 of the handle unit 2, so that the rear-end side periphery section 87 of the rotor 78 is fitted in the bore 58 of the stopper receiving member 56 of the transducer unit 4.

Figure 6A:
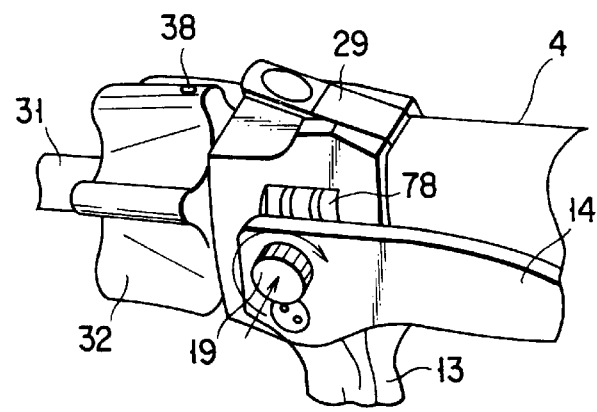
FIGS. 6A and 6B are perspective views showing the handle unit.
Figure 6B:
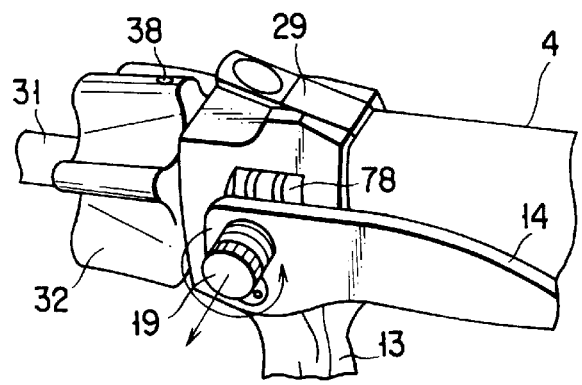

Finally, as shown in FIG. 6A, the externally threaded section 26 is inserted into the internally threaded section 25 while pushing the fixed screw member 19. Then the engaging section 21 is fitted in the annular groove 82 of the rotor 78, so that the rear-end handle 14 is connected to the rotor. The jaw holding member 100 of the probe unit 3 is latched to the paired latching pieces 36 at the distal end of the insertion section inside areas and their relative rotation about the axis is prevented and their integral rotation is ensured.

Figure 18A:
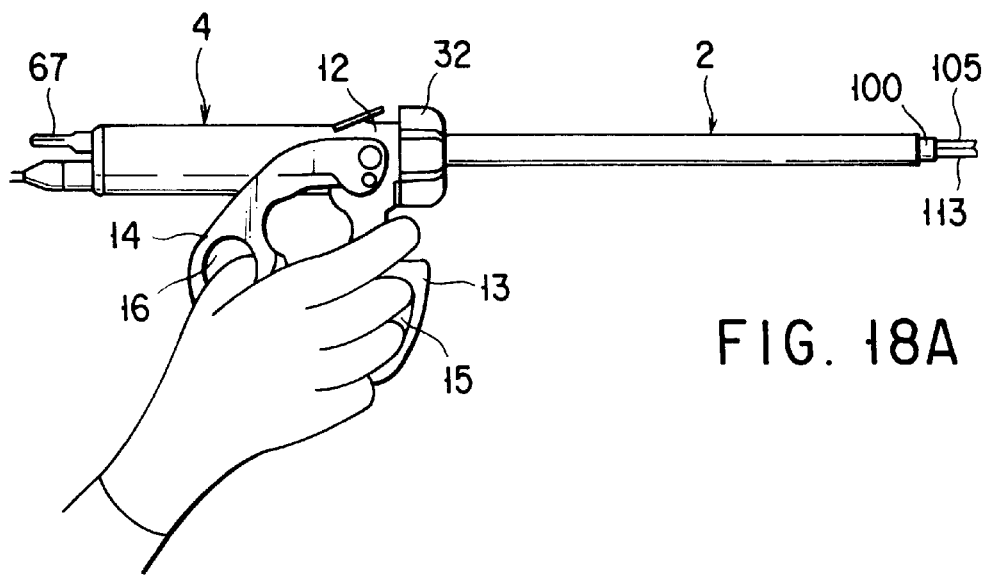
FIG. 18A is an explanatory view showing an example of a grasping operation by the apparatus.
Figure 18B:
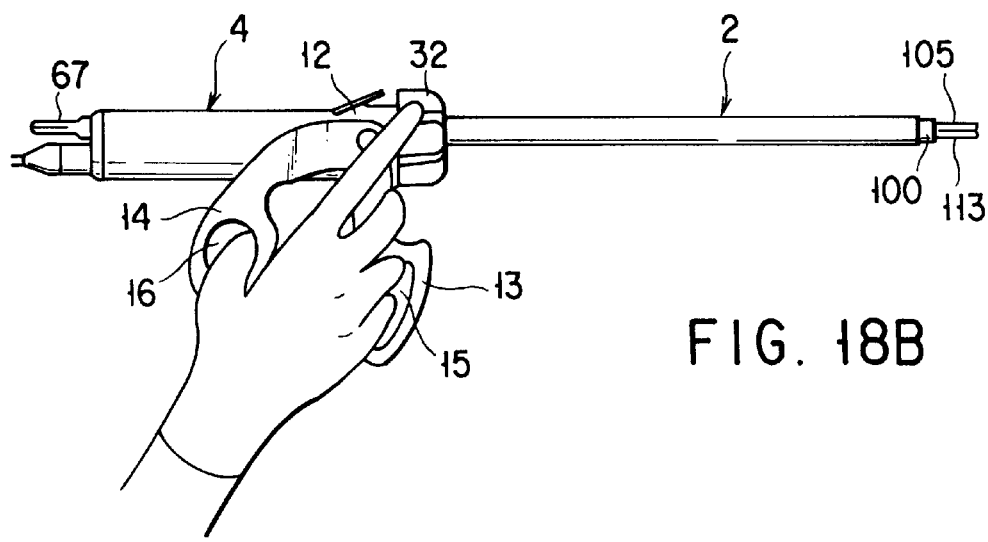
FIG. 18B is an explanatory view showing another example of a grasping operation by the apparatus.

As shown in FIG. 18, when the rear-end handle 14 is rotated with the respective handles 13, 14 of the handle unit 2 hand-gripped, the jaw 105 is rotated to allow the opening/closing of the distal end treating section. When the rear-side handle 14 is rotated, the jaw 105 is rotated relative to the fixedly positioned probe 113, so that a living tissue can be grasped between the two. Further, with the jaw in an open state, it is possible to separate the organ apart from its position and push/displace it. The handles 13, 14 can be gripped by two methods for example, one as shown in FIG. 18A and the other as shown in FIG. 18B. In the gripping method as shown in FIG. 18B, the rotation knob 32 is rotated by the forefinger whereby it is possible to rotationally operate both the rotation unit 3 and transducer unit 4.

When a treatment is to be made with the ultrasonic wave, the insertion sheath section 31 is guided into the body cavity of the subject by utilizing a trocar, etc., and the living tissue of interest is grasped between the jaw 105 and the probe of the distal-end processing section. If, at this time, an ultrasonic vibration is applied to the probe 113, the grasped tissue is cut while being coagulated. At this time, the jaw 105 is moved into a closing position and, during a process of holding the tissue between the probe 113 and the jaw 105, the stopper mechanism acts, so that it is possible to grasp the tissue with a proper holding amount without involving any excessive grasping force. That is, the jaw is moved into a closing position by the pulling of the operation drive rod 72. This gradually narrows the gap between the jaw 105 and the probe 113 and applies a greater force to the grasping living tissue. At a time of obtaining a predetermined grasping power, the rear end of the stopper tube 121 abuts against the stopper receiving face 125 and any further backward movement of the operation drive rod 72 is blocked. As a result, the further closing of the jaw 105 is prevented, thus applying no further strong grasping force to the living tissue.

Thus the pressing force of the jaw 105 on the probe 113 is prevented by the stopper mechanism and is suppressed in a predetermined grasping level range. Even if, therefore, the handles are hand-gripped with the greatest possible force or even if any excessive operation force is inadvertently applied to the handles due to the difference in experience or skill between individual to individual, the tissue is normally cut while being coagulated. And there is no risk that the living tissue, such as a minute blood vessel, will be cut off simply mechanically. Thus, no higher and delicate hand-grip technique is required on the part of the operator and it is possible to positively cut off the living tissue, while being coagulated, in spite of the operation being easier and simpler. Further, without depending upon the difference in experience or skill between operator to operator, it is possible to perform treatment in a stabler and optimal state, any time, and to do so with no fear.

Since the living tissue of interest can be grasped, at an optimal grasping force, between the jaw 105 and the probe 113, a stabler coagulating/cutting treatment can be positively effected under an ultrasonic vibration and do so positively. Therefore, there occurs neither the situation under which no desired effective treatment is effected due to no adequate heat generation of the ultrasonic vibration of the probe 113 nor the situation under which the ultrasonic vibration at the probe 113 is stopped with an excessive force either under a varying grasping amount or under a varying heat generation amount. Since no such unexpected situation occurs, the handles can be positively hand-gripped without any particular care and, under the function of the stopper mechanism, the living tissue of interest can be gripped with an optimal grasping force at all times.

In the stopper mechanism, the stopper tube 121 is fixed to an intermediate portion of the operation drive rod (movable member) 72 connected to the jaw 105 and the rear-end of the stopper 121 abuts against the stopper receiving face 125 of the jaw holding member 100 serving as a stationary member. These stopped function members each are assembled in the arrangement of the probe unit 3, in particular, at the location of the jaw holding member 100. Therefore, less other members are present from the stress mechanism to the jaw 105. As a result, there is less of an adverse effect resulting from an additive combination of the manufacturing errors among component parts and assembling error of the associated units and from a warp and expansion/contraction of those intervening members. It is, therefore, possible to exactly stop the jaw 105 to an originally intended position. That is, it is possible to exactly set a grasping force amount in a required range without deviating from the rotation stop position of the jaw 105 and to positively coagulate/cut the living tissue of interest.

Assuming that the probe 113 is not entirely moved and stays in a fixed position, the above-mentioned function can also be obtained in the case where the probe 113 is elastically deformed/displaced.

In the latter case where the probe 113 is elastically deformed, it is possible to obtain not only the above-mentioned function but also the following function. That is, since the probe 113 is provided on a distal end (free end) of the vibration transmitting member 71, if the probe 113 is pressed by the tissue grasping jaw 105 in the case where the tissue is grasped between the probe 113 and the jaw 105, then the free end portion of the vibration transmitting member 71 is flexed while the probe 113 follows the grasping surface of the jaw 105, and is displaced. The position of the probe 113 as indicated by a solid line in FIG. 8A shows the displaced position and the position of the probe 113 as indicated by a dot-dash line shows a not-displaced position. In the case where the living tissue is grasped, the probe 113 is so displaced as to follow the surface of the jaw 105 and no excessive grasping force acts between the jaw 105 and the probe 113, so that the living tissue is grasped by a necessary force in a stable fashion.

Further, the biting/grasping relation of the jaw 105 and probe 113 is such that the grasping surface of the jaw 105 is normally set in contact with the grasping surface of the probe 113 in which the latter is not displaced. When the jaw 105 is further rotated by a given amount from the grasping/biting contact position between the jaw 105 and the probe 113, then the stopper mechanism functions and further rotation of the jaw 105 is blocked. By this setting, the grasping force between the jaw 105 and the probe 113 becomes stable in accordance with a following displacement of the probe 113. At the same time, the jaw 105 and probe 113 are maintained in a proper biting/grasping position. If, for example, the jaw 105 is moved excessively toward the probe 113, then their grasping surfaces cease to be parallel to each other and are diagonally contacted with each other, so that the grasping surfaces are not uniformly contacted. However, such an excessive rotation of the jaw 105 is blocked under the action of the stopper mechanism 105 and such an inconvenience is avoided. This obviates the need to make the probe 113 and vibration transmitting member 71 thicker and it is possible to construct a compact treating section.

Further, since the hole 106 of the jaw 105 is formed as the elongated hole and the pivotal pin 103 can be slidably moved along the elongated hole 106, the following function can be obtained. First, by the pulling of the operation drive shaft, the jaw 105 starts to be rotated and the grasping state continues. This operation process will be explained below. First, the jaw 105 starts to be closed by pulling of the operation drive shaft 72. Since the distal end portion of the operation drive shaft 72 is elastically bent down (it may not be of a bent-down type but here it is allowed to be bent down), when the jaw 105 is opened, the pivotal pin 103 is situated at the bottom end of the hole 106 of the jaw 105 as shown in FIG. 12A. Therefore, the jaw 105 is readily moved away from the bottom-side probe 113 and it is possible to design a compact treating section.

When the jaw 105 is rotated from an open position as shown in FIG. 12A to a position as shown in FIG. 12B, the jaw grasps the living tissue. In this initial grasping position, the pivotal pin 103 is situated at the bottom end of the hole 106 in the jaw 105. After the living tissue is adequately grasped between the jaw 105 and the probe 113, the pivotal pin 103 is slidably moved to allow the pivotal pin 103 to reach the top end of the hole 106 in a final grasping position as shown in FIG. 12C. In an open state, the distal end portion of the operation drive shaft 72 is elastically bent down to allow the jaw 105 to be pushed up. As a result, the pivotal pin 103 is situated on the bottom side of the hole 106. And the full length of the hole 106 from the bottom to the top provides a slide effective range of the bent portion 107 and a stable grasping operation is ensured.

Since the pivotal pin 103 is slidable in the hole 106 of the jaw 105, the grasping surfaces of the jaw and probe stay in a long contacted state in a substantially parallel relation to ensure an improved grasping state of the jaw and probe. Further, more tissue can be grasped between the jaw and the probe and, even if a tissue grasping amount is greater, the tissue of interest can be grasped uniformly.

Since, in particular, the longitudinal direction of the hole 106 is inclined at the angle θ in a plane perpendicular to the hole 106 side and relative to the grasping surface of the probe 113, the pivotal pin can be smoothly moved in slide motion, thus ensuring a smooth operation of the jaw 105. If the longitudinal direction of the hole 106 is so defined at the angle θ, the grasping of the jaw relative to the probe is improved and their grasping contact at the closing of the jaw is made wholly uniform and the tissue grasping can be further improved.

Further, the inclined angle θ is set to be 0°<θ<90°. Normally, a greater grasping quantity is involved at the base end side, but, if the inclined angle θ is set to be 12°±10° in particular, a substantially equal grasping amount is obtained both at the distal-end side and at the base end side. Even if, therefore, the tissue is grasped at the distal end portion, it will not drop.

Figure 19:
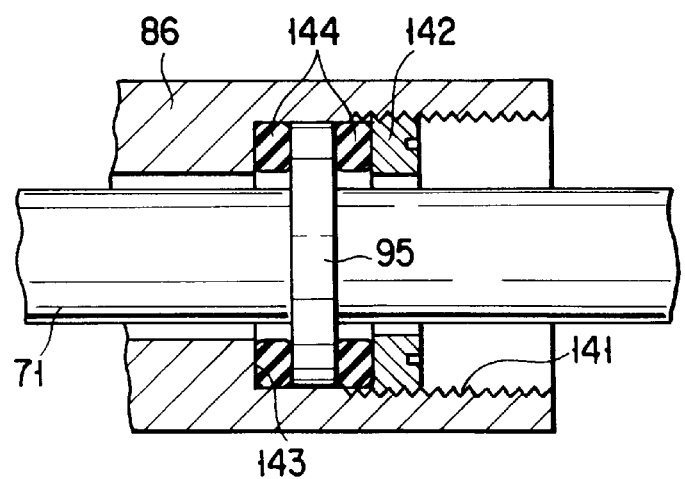
FIG. 19 is a cross-sectional view showing the fitting of a spacer over a vibration transmitting member.

In the above-mentioned embodiment, the forwardest spacer 86 may be mounted as shown in FIG. 19. A hole 141 is provided in the spacer 86 and a flange 95 of the vibration transmitting member 71 is fitted in the hole 141. A holding nut 142 is threaded in the hole 141. A vibration absorbing member, such as a rubber cushion 144, is interposed in the hole 141 at an area between an inner face 142 of the hole 141 and flange 95 and at an area between the flange 95 and the nut 142 and, in this state, the vibration absorbing member is fixed in place by means of the nut 142.

The final position when the operation drive rod 72 and rotor 78 are retracted is determined by abutting the rear end of the rotor 78 against the forward end of the stopper receiving member 56 of the transducer unit 4. A slide quantity L is determined in a relation between the rear end of the rotor 78 and the stopper receiving member 56 (see FIG. 14).

The stopper mechanism for restricting the rotation amount of the jaw 105 may be so constructed as set out below. This is, the stopper mechanism may comprise a connection member, such as the rotor 78, coupled to the rear end of the operation drive rod 72 of the probe unit 3 and adapted to be moved by the operation of the handles on the handle 2 side and a fixed member, such as the stopper receiving member 56, confronting the rotor 78 and regarded as a stationary member when being relatively viewed and, in this mechanism, the opening/closing position of the jaw 105 relative to the probe 113 is restricted by abutting the rear end of the rotor 78 against the forward end of the stopper receiving member 56 and, by doing so, restricting the movement of the operation drive rod 72.

The stopper mechanism may also be provided by providing a stopper provided on one handle of the handle unit relative to the other handle and, by doing so, the opening/closing terminal position of the jaw 105 relative to the probe 113 is restricted. As shown in FIG. 17, for example, a stopper 150 is provided on a rear-end handle (movable-side handle) 14 so that it can be abutted against a stopper receiving section provided on a support member, such as the operation body 12 and front-end handle 13, for supporting the rear-end handle.

Additional advantages and mod fictions will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic surgical apparatus for treating a tissue of interest by applying an ultrasornic vibration to the tissue while grasping the tissue between an ultrasonic probe and a jaw, comprising:

an ultrasonic transducer provided in a housing and generating an ultrasonic vibration;

a vibration transmitting member connected to the ultrasonic transducer to transmit the ultrasonic vibration;

an ultrasonic probe connected to the vibration transmitting member;

a movable jaw mounted relative to the probe and, together with the probe, being adapted for grasping the tissue;

a movable member being operated to move the movable jaw;

a support member movably supporting the movable member; and a stopper for stopping in cooperation with the movable member and the support member, the movable jaw in a terminal position thereof when the movable jaw is moved toward the probe, thereby restricting a tissue grasping force of the movable jaw when the movable jaw grasps the tissue.

2. The apparatus according to claim 1, wherein the stopper comprises a stopper body mounted on the movable member and a stopper receiving section.

3. The apparatus according to claim 2, further comprising adjusting means mounted on the movable member to adjust a position of the stopper.

4. The apparatus according to claim 3, wherein the adjusting means adjusts the position of the stopper body by threadably inserting the stopper body into the movable member and, by doing so, changing a threaded position.

5. The apparatus according to claim 4, further comprising a nut threaded over the movable member to fix the position of the stopper body.

6. The apparatus according to claim 1, wherein, when the tissue is grasped between the movable jaw and the probe, the probe is elastically deformed in accordance with a grasping force and displaced in a way to follow a position of the movable jaw in which a required grasping force is stably applied to the tissue.

7. An ultrasonic surgical apparatus for treating a tissue of interest by applying an ultrasonic vibration to the tissue while grasping the tissue between an ultrasonic probe and a jaw, comprising:

an ultrasonic transducer provided in a housing and generating an ultrasonic vibration;

a vibration transmitting member connected to the ultrasonic transducer to transmit the ultrasonic vibration;

an ultrasonic probe provided at a far end of the vibration transmitting member;

a movable jaw mounted opposite to the probe and, together with the probe, being adapted for grasping the tissue;

a jaw holding member movably supporting the movable jaw and having a stopper receiving section;

a movable member being operated to move the movable jaw; and a stopper body mounted on the movable member and adapted to, when the tissue is grasped, abut against the stopper receiving section to restrict a terminal position of a movement of the movable jaw relative to the probe, whereby a tissue grasping force is restricted.

8. The apparatus according to claim 7, wherein the movable jaw is pivotally connected by a pin to the jaw holding member.

9. The apparatus according to claim 8, wherein the pin is freely movably pivoted in an elongated hole in a pin receiving member along a longitudinal direction of the elongated hole.

10. The apparatus according to claim 9, further comprising means for elastically urging the movable jaw in a direction to move the pin along the longitudinal direction of the elongated hole.

11. The apparatus according to claim 10, wherein the means for elastically urging the movable jaw utilizes an elastic deformation of the movable member.

12. The apparatus according to claim 9, wherein the longitudinal direction of the elongated hole is inclined with respect to a line normal to a grasping surface of the probe.

13. The apparatus according to claim 12, wherein an angle between the longitudinal direction of the elongated hole and the line normal to the grasping surface of the probe is at most 45°.

14. An ultrasonic surface apparatus for treating a tissue of interest while grasping the tissue between an ultrasonic probe and a jaw, comprising:

an ultrasonic transducer provided in a housing and generating an ultrasonic vibration;

a vibration transmitting member connected to the housing to transmit the ultrasonic vibration;

an ultrasonic probe connected to the vibration transmitting member;

a movable jaw mounted relative to the probe so that the tissue of interest can be grasped between the movable jaw and the probe;

handle means having a movable member for moving the movable jaw and being adapted to operate the movable member;

a stopper restricting a movement of the handle means so as to determine a terminal position of a movement of the movable jaw in a direction where the movable jaw is moved toward the probe whereby a force for grasping the tissue by moving the movable jaw relative to the probe is restricted.

15. An ultrasonic surgical apparatus for treating a tissue of interest while grasping the tissue between an ultrasonic probe and a jaw, comprising:

a transducer unit containing ultrasonic vibration elements;

a probe unit including a probe connected to the ultrasonic vibration elements, a movable jaw mounted relative to the probe, and a jaw holding member for holding the movable jaw, a movable operation body connected to the movable jaw, and being adapted to grasp the tissue between the movable jaw and the probe;

a handle unit including handle means for operating the movable jaw through the movable operation body;

a support member movably supporting the movable operation body; and a stopper for stopping in cooperation with the movable operation body and the support member, the movable jaw in a terminal position thereof when the movable jaw is moved toward the probe, thereby restricting a tissue grasping force of the movable jaw which acts when the movable jaw grasps the tissue.

* * * * *